United States Patent [19]

Robioneck et al.

[11] Patent Number: 5,643,258

[45] Date of Patent: Jul. 1, 1997

[54] DEVICE FOR STABILIZING LONG BONES

[75] Inventors: Bernd Robioneck, Preetz, Germany; Giuseppe Varlaro, Pordenone, Italy

[73] Assignee: Howmedica GmbH, Schönkirchen, Germany

[21] Appl. No.: 506,455

[22] Filed: Jul. 24, 1995

[30] Foreign Application Priority Data

Aug. 10, 1994 [DE] Germany .......................... 94 12 873.1

[51] Int. Cl.⁶ .................................................. A61B 17/56
[52] U.S. Cl. .................. 606/54; 606/59; 606/68; 606/63
[58] Field of Search .................. 606/53, 54, 55, 606/56, 57, 58, 59, 60, 62, 63, 64, 65, 66, 67, 68

[56] References Cited

U.S. PATENT DOCUMENTS

| 2,821,979 | 2/1958 | Cameron | 128/92 |
| 4,281,649 | 8/1981 | Derwedowen | 128/92 |
| 4,875,474 | 10/1989 | Border | 128/92 |
| 4,875,475 | 10/1989 | Comte et al. | 128/92 |

FOREIGN PATENT DOCUMENTS

WO9100065  1/1991  European Pat. Off. .

Primary Examiner—Michael Buiz
Assistant Examiner—Mark S. Leonardo
Attorney, Agent, or Firm—Peter C. Richardson; Lawrence C. Akers; Raymond W. Augustin

[57] ABSTRACT

A device for stabilizing a long bone combines an external fixator with a locking nail implanted in the medullary canal of a long bone. The external fixator has fixed bone pins at each of its ends and movable bone pins intermediate its ends. The fixed bone pins extend through transverse bores at each end of the bone nail and the movable pins extends through a slot in the bone nail intermediate its ends. By this method a fracture can be compressed and stabilized while healing.

9 Claims, 3 Drawing Sheets

DEVICE FOR STABILIZING LONG BONES

BACKGROUND OF THE INVENTION

1. Field of the Invention

The invention relates to a device for stabilizing long bones, especially after the removal of a bone segment.

2. Description of the Prior Art

Locking nails for the stabilization of fractured long bones have been developed in many different embodiments. They are proximally or distally driven into a long bone and, in most cases, comprise transverse through bores for a bone screws at their ends. This allows both sides of the fracture and any bone fragments to be connected to the locking nail with the aid of bone nails or screws to provide rotational stability.

DE 39 28 460 shows a locking nail where the distal through bore of the locking nail is defined as an elongated hole. In addition, U.S. Pat. Nos. 4,281,649 and 4,875,475 teach to form the through bore as an elongated hole or slot within the proximal area and to put a pressure on the bone nail with the aid of a threaded pin screwed into the proximal end so as to in this way obtain a compression.

WO 91100065 also shows a similar compression device in connection with a locking nail. There it is shown that the hollow locking nail receives an inner part so as to be secured against torsion. The inner part is longitudinally displaced and can be axially moved from its proximal position. A through bore is provided which cooperates with an elongated hole in the nail. A corresponding bone screw can be led through the bore within the inner part. The device described is used for an osteotomy and allows the edges of the osteotomy to move apart from each other by a longitudinal displacement of the inner part.

DE 35 37 318 relates to a sliding slotted nail which has proximal and distal slots in a cloverleaf-shaped nail profile. The nail profile comprises an open through slot of a Küntscher-type nail. Using such a nail it is possible to drive in the locking screws without using any aiming devices and image converters.

U.S. Pat. Nos. 4,877,019, 4,475,545 and 5,034,013 relate to locking nails which include an elongated hole or slot on one side only.

Furthermore, it is known to use an external fixator for stabilizing bones. It comprises a support element adapted to be provided at the outside of the bone and includes a plurality of adjustable pins which can be driven transversely across the bone. Such an external fixator can also be used for an osteotomy, ie., where a bone segment is removed. With the aid of a suitable structure, a pin arranged on the support element can be moved in parallel so as to realize a compression or displace a bone segment.

SUMMARY OF THE INVENTION

It is the object of the invention to provide a device for stabilizing long bones, especially when an osteotomy is performed, which particularly advantageously combines a locking nail and an external fixation device.

According to the present invention, the marrow area locking nail which at its ends is provided with through bores in a known manner comprises at least one elongated through slot for receiving bone screws. This slot receives at least one pin of an external fixation device. In this way, the pin of the external fixator is externally stabilized and can move only within the area of the nail with the slot. In addition, the slot acts as a guide for the pin of the external fixator in case of any movement of the bone segment.

In one embodiment two slots which are located in series at opposite ends of the nail are slightly spaced apart from each other. Thus, the weakening of the locking nail which automatically occurs as a result of such an elongated through slot in the center area is slightly reduced. Preferably, the slots are provided on approximately the same plane as the through bores for the bone nails so that the slot and holes extend in a parallel direction.

According to a further embodiment of the invention, a hollow locking nail may be used. It includes a circumferentially extending wall and comprises a cloverleaf-shape cross-sectional profile. The cloverleaf-shape profile gives the locking nail a very high geometrical moment of inertia which means that it has a high transverse stability and/or rotational stability. This can compensate for the weakening caused by the slot. Preferably, a cylindrical tube is used as the basic material for the locking nail which at circumferential distances of 120° is radially pressed inwardly so as to obtain the cloverleaf-shape profile.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
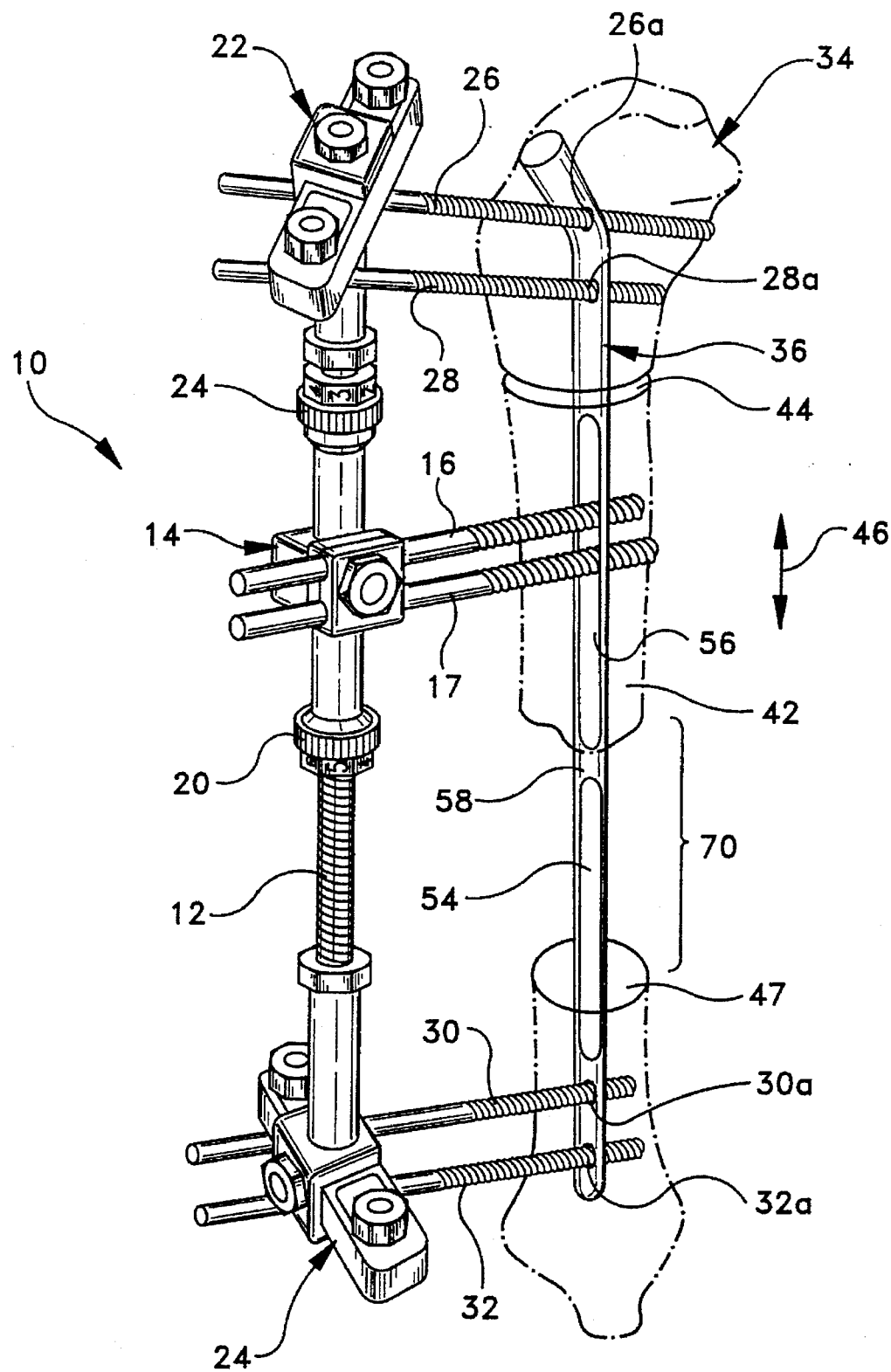
FIG. 1 is a perspective view of the combination of an external fixation device and a locking nail according to the invention after implantation of the nail.

The fixation device 10 shown in FIG. 1 comprises a threaded spindle 12 on which a first centrally located supporting element 14 is displacably mounted. First supporting element 14 supports two bone pins 16, 17 which may be displaced in a proximal-distal direction by moving the knurled nuts 18 and 20 respectively. The displacement is shown by a double arrow 46 in FIG. 1. A second and a third supporting element, 22 and 24 respectively, are mounted at opposite ends of spindle 12. Each supporting element 22 and 24 supports a pair of bone pins 26, 28 and 30, 32 respectively. The mounting of bone pins 16, 17, 26, 28, 30 and 32 may be in any known manner used in the external fixation art which allows the pins to be fixed in any angular position whatever.

Also referring to FIG. 1, a locking nail 36 is shown driven into a long bone such as tibia 34 usually from a proximal position. In the preferred embodiment both the proximal and the distal end of the locking nail have transverse through bores 26a, 28a, 30a and 32a for receiving bone screws or the threaded pins 26 to 32. The insertion of the threaded pins makes the use of a suitable aiming device necessary which often includes an image intensifier. Such aiming devices are well known and are not shown in FIG. 1. In the preferred embodiment adjustable bone pins 16, 17 extend through a longitudinal slot 56 of locking nail 36 into bone segment 42.

As shown in FIG. 1, a bone segment 42 has been separated by a pair of cuts 44 and 47. Furthermore, the bone 34 had been distracted so as to form a recess 70. Thereafter, as a result of the downward movement of the support element 14, bone segment 42 is moved downwardly in the direction of closing recess 70. This is done by the rotation of knob 20 as will be better described below. This movement causes the bone pins 16, 17 to move within the area of the slot 56 of the locking nail 36. The free space which opens up at cut 44 above the segment 42 may be filled with bone graft substance.

In use, rod 36 is driven into the canal of a long bone which is either fractured or from which a cancerous section of bone has been removed. Threaded pins 26 to 32 are then placed through holes 26a to 32a in rod 36 by any known method. External fixation device 10 is then mounted adjacent to nail 36 on pins 26 to 32.

Threaded pins 16 and 17 are then threaded through slot 56 in nail 36 into bone segment 42. The location of pins 16 and 17 and thereby the location of bone segment 42 can be adjusted by moving the first supporting element along thread rod 12 by adjusting nuts 18 and 20. The resultant gap at cut 42 and the recess 70 may be filled with bone graft material to promote healing.

Figure 2:
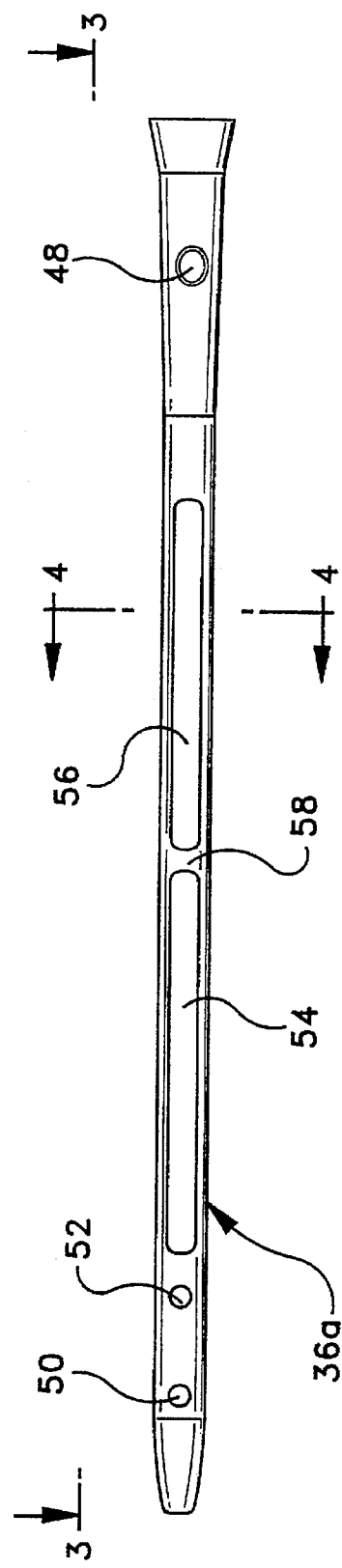
FIG. 2 is a side view of the locking nail according to FIG. 1.
Figure 3:
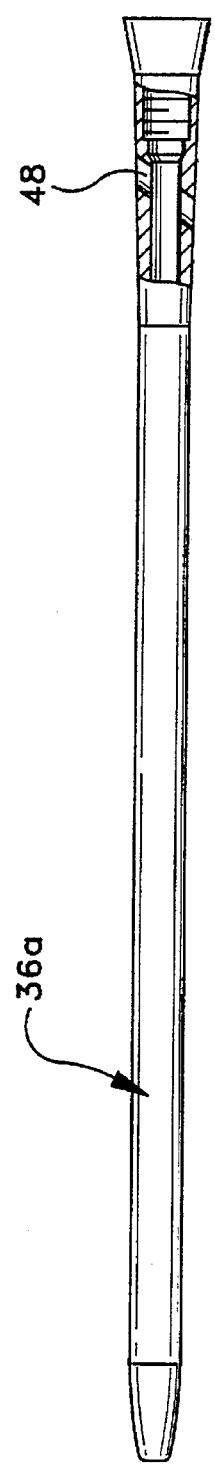
FIG. 3 is a second side of FIG. 1 rotated 90° with respect to the side view of FIG. 2.
Figure 4:
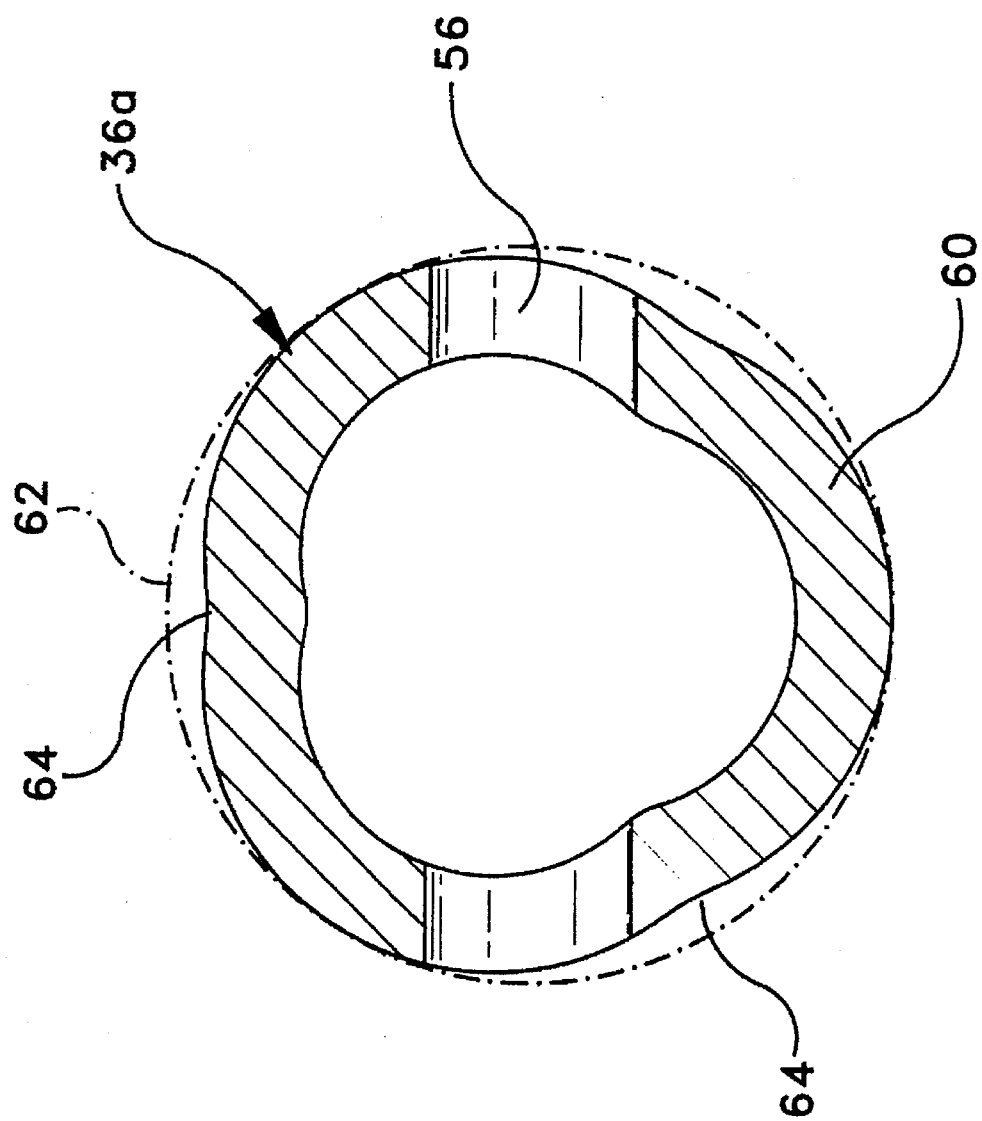
FIG. 4 is a cross-sectional view of the nail according to FIG. 3 taken along line 4—4.

Referring to FIGS. 2 through 4 there is shown a locking nail designed for use in the femur which is similar in construction to the locking nail of FIG. 1. It, therefore, has been provided with the reference number 36a. The hollow nail 36a at the proximal end comprises an included through bore 48 and at the distal end includes two circular spaced through bores 50, 52 for the threaded pins mentioned in connection with FIG. 1. Moreover, in the center area the shaft comprises two longitudinal slots 54, 56 which are separated from each other by a relatively narrow space 58. The lengths over which both slots 54, 56 extend approximately correspond to half the length of the complete nail 36a with the distance between the distal end of the slot 54 and the distal nail end being smaller than the distance between the proximal end of the slot 56 and the proximal nail end. The width of the slots 54, 56 is slightly larger than the diameter of the bores 50, 52.

As shown in FIG. 4, hollow nail 36a includes a circumferential wall 60. The nail is first formed of a cylindrical tube as shown by the dash-dot line 62. It then is radially pressed inwardly in positions being offset by 120° as shown at 64 so as to get a cloverleaf-shape profile which increases the stability of the nail 36a in transverse and circumferential direction. Such a nail, of course, could be used in any long bone in the manner described in connection with the implantation of the nail shown in FIG. 1.

While several examples of the present invention have been described, it is obvious that many changes and modifications may be made thereunto, without departing from the spirit and scope of the invention.

We claim:

1. A device for stabilizing long bones comprising:

an external fixator comprising a longitudinally extending support rod to be spaced from and parallel to said long bone, at least three pins transversely mounted in series to said support rod along the length thereof, at least one of said pins located on said support rod intermediate two of said at least three pins being movable in a longitudinal direction; and a locking nail for mounting in the medullary canal of said long bone which has at each of its ends at least one transverse through bore for receiving at least one of said at least two pins, and having between the ends of said nail at least one elongated longitudinally extending transverse through slot for receiving said at least one movable pin.

2. The locking nail of claim 1 wherein said at least one elongated slot includes two transverse slots provided adjacent the ends of said nail, said slots separated from each other by a solid nail portion.

3. The locking nail of claim 1 wherein said through bores and said at least one elongated slots through said nail extend transversely through said nail parallel to each other.

4. The locking nail of claim 3 wherein said locking nail has a hollow body which comprises a circumferentially extending wall and said slot extends through opposite sides of said circumferentially extending wall.

5. The device of claim 1 wherein said two of said at least three pins are in a fixed position on said rod and extend through holes in said rod, said at least one movable pin is mounted on said support rod and extends through said elongated longitudinal slot in said locking nail.

6. The device of claim 1 wherein at least one of said at least two pins are fixed with respect to said longitudinally extending support rod.

7. The device of claim 1 wherein each of said at least two pins are fixed to said longitudinally extending support rod.

8. The device of claim 1 wherein said longitudinally extending support rod has a threaded portion.

9. The device of claim 8 wherein said at least one moveable pin is mounted on a threaded support element operatively engaging said threaded portion so that rotation of said support rod causes movement of said pin between said at least two fixed pins.

* * * * *